US008304748B2

(12) United States Patent
Derenzo et al.

(10) Patent No.: US 8,304,748 B2
(45) Date of Patent: Nov. 6, 2012

(54) IDENTIFYING NEW SEMICONDUCTOR DETECTOR MATERIALS BY D.C. IONIZATION CONDUCTIVITY

(75) Inventors: Stephen E. Derenzo, Pinole, CA (US); Edith Bourret-Courchesne, Berkeley, CA (US); Yetta D. Porter-Chapman, Pittsburg, CA (US); Floyd J. James, Jamestown, NC (US); Mattias K. Klintenberg, Uppsala (SE); Jie Wang, Shanghai (CN); Jia-Qing Wang, legal representative, Shanghai (CN)

(73) Assignee: The Regents of the University of California, Oakland, CA (US)

( * ) Notice: Subject to any disclaimer, the term of this patent is extended or adjusted under 35 U.S.C. 154(b) by 987 days.

(21) Appl. No.: 12/091,045

(22) PCT Filed: Oct. 19, 2006

(86) PCT No.: PCT/US2006/060087
§ 371 (c)(1),
(2), (4) Date: Dec. 23, 2008

(87) PCT Pub. No.: WO2007/048116
PCT Pub. Date: Apr. 26, 2007

(65) Prior Publication Data
US 2009/0212395 A1 Aug. 27, 2009

Related U.S. Application Data

(60) Provisional application No. 60/729,161, filed on Oct. 21, 2005.

(51) Int. Cl.
*A61N 5/00* (2006.01)
*G21G 5/00* (2006.01)
(52) U.S. Cl. ..................... 250/492.1; 250/351
(58) Field of Classification Search .................. None
See application file for complete search history.

(56) References Cited

U.S. PATENT DOCUMENTS 3,453,431 A * 7/1969 Lederhandler ............... 250/351
4,602,422 A   7/1986 Dinh
(Continued)

OTHER PUBLICATIONS

Pozynyak, S. K. and A. I. Kulak, "Photoelectrochemical Properties of Bismuth Oxyhalide Films", Electrochimica Acta, vol. 35, No. 11/12, pp. 1941-1947 (1990).*

(Continued)

*Primary Examiner* — Jessica L Ward
*Assistant Examiner* — Ross J Christie
(74) *Attorney, Agent, or Firm* — Robin C. Chiang; Fernando Santos; Lawrence Berkeley National Laboratory (57) ABSTRACT

Herein is described a method for identifying semiconductor radiation detector materials based on the mobility of internally generated electrons and holes. It was designed for the early stages of exploration, when samples are not available as single crystals, but as crystalline powders. Samples are confined under pressure in an electric field and the increase in current resulting from exposure to a high-intensity source of ionization current (e.g., $^{60}Co$ gamma rays) is measured. A pressure cell device is described herein to carry out the method. For known semiconductors, the d.c. ionization current depends on voltage according to the Hecht equation, and for known insulators the d.c. ionization current is below detection limits. This shows that the method can identify semiconductors in spite of significant carrier trapping. Using this method and pressure cell, it was determined that new materials BiOI, PbIF, $BiPbO_2Cl$, $BiPbO_2Br$, $BiPbO_2I$, $Bi_2GdO_4Cl$, $Pb_3O_2I_2$, and $Pb_5O_4I_2$ are semiconductors.

9 Claims, 6 Drawing Sheets

U.S. PATENT DOCUMENTS 5,972,428 A 10/1999 Hayashi et al.
2001/0047728 A1 12/2001 Brandtjen, Jr. et al.

OTHER PUBLICATIONS

Patel, S.G. "Applications of Semiconductor Laser in High Pressure Studies", Proceedings of SPIE, vol. 4913 (2002) pp. 1-10.*

PCT/US06/60087 Written Opinion.

Armantrout, et al., "What can be expected from high-Z semiconductor detectors?," IEEE Trans Nucl Sci, vol. NS-24, pp. 121-125, 1977.

Derenzo, et al., "Identifying Semiconductors by D.C. Ionization Conductivity", IEEE Nucler Science Symposium Conference Record 1132-1134 Oct. 23-29, 2005.

Derenzo, et al., "Temperature dependence of the fast, near-band-edge scintillation from CuI, HgI2, PbI2, ZnO:Ga, and CdS:In," Nucl Instr Meth, vol. A486, pp. 214-219, 2002.

Derenzo, et al., "Scintillation studies of CdS(In): effects of codoping strategies," Nucl Instr Meth, vol. A537, pp. 261-265, 2005.

Gavartin, et al., "Modeling charge self-trapping in wide-gap dielectrics: localization problem in local density functionals," Phys Rev B, vol. 67, pp. 035108-8, 2003.

Manfredotti, R. Murri, A. Quirini, et al., "PbI2 as a nuclear particle detector," IEEE Trans Nucl Sci, vol. NS-24, pp. 126-128, 1977.

Shah, J. C. Lund, F. Olschner, et al., "Thallium bromide radiation detectors," IEEE Trans Nucl Sci, vol. NS-36, pp. 199-202, 1989.

Strehlow, et al., "Compilation of energy band gaps in elemental and binary compound semiconductors and insulators," J Phys Chem Ref Data, vol. 2, pp. 163-199, 1973.

Valentine, et al., "Temperature dependence of CsI(Tl) gamma-ray scintillation decay time constants and emissions spectrum," Nucl Instr Meth, vol. A325, pp. 147-157, 1993.

Wang, et al., "High conductivity in gallium-doped zinc oxide powders," Chem Mater, vol. 8, pp. 433-43WANG, et al., "High conductivity in gallium-doped zinc oxide powders," Chem Mater, vol. 8, pp. 433-439, 19969, 1996.

* cited by examiner

IDENTIFYING NEW SEMICONDUCTOR DETECTOR MATERIALS BY D.C. IONIZATION CONDUCTIVITY

CROSS-REFERENCE TO RELATED APPLICATIONS

This application is the National Stage application under 35 U.S.C. 371 of PCT Application No. PCT/US2006/60087 filed on 19 Oct. 2006 which claimed priority to U.S. Provisional Patent Application 60/729,161, filed 21 Oct. 2005, both of which are hereby incorporated by reference in their entirety.

STATEMENT OF GOVERNMENTAL SUPPORT

This work was supported by U.S. DOE Contract DE-AC02-05CH11231 and NIBIB Public Health Service Grant R01 EB00339. The government has certain rights in this invention.

BACKGROUND OF THE INVENTION

1. Field of the Invention

The present invention relates to methods and devices for the discovery and identification of new semiconductor materials as detector materials, and semiconductor materials which have been identified using these methods.

2. Description of the Related Art

The discovery of new semiconductors triggers new applications in fields as diverse as optoelectronics, sensors, detectors and power electronics. The exploration for new semiconductor materials increases the chances of finding a heavy-atom compound that can be grown as large crystals with little carrier trapping. It well may be that the current list of known compounds (e.g. $HgI_2$, $PbI_2$, CZT, TlBr, AlSb) does not contain the best possible materials. Furthermore new materials may become candidates for heavy-atom, ultra-fast, luminous semiconductor scintillators and allow radiative transition [e.g. donor band-acceptor CdS(In, Te)] and have a small band gap such as 200,000 photon/MeV limit.

While it is generally recognized that materials with a small band gap are semiconductors and those with a large band gap are insulators, there are notable exceptions, such as diamond. X-ray diffraction measurements have been made for over 100,000 crystalline materials and the results fill the Inorganic Crystal Structure and Powder Diffraction Databases, but bandgaps have been measured for only a small percentage of them. Even so, the bandgap alone is not a useful characteristic for identifying semiconductors because the bandgap range between 1.5 and 3.5 eV that contains many useful semiconductors also contains insulators. A temperature-dependent electrical conductivity is not useful for identifying semiconductors because only semiconductors with bandgaps below 1.5 eV exhibit appreciable thermal ionization at reasonable temperatures. Furthermore, temperature-dependent electrical conductivity is not useful because it is negligible in undoped semiconductors with band gaps above 1.5 eV but can be large for insulators that exhibit ionic conductivity. For example NaCl is not a semiconductor because holes are spontaneously trapped on the $Cl_2^-V_k$ center but the electrical conductivity is high due to motion of the $Cl^-$ ions. Moreover, many insulators have large ionic conductivities that increase with temperature.

A successful semiconductor radiation detector material should have good stopping power, can be obtained as large crystals at low cost, have acceptable carrier mobilities and lifetimes, and operate at ambient temperatures. Despite the fact that available detector materials fall short of these goals, the list of candidate materials has not grown substantially during the past 25 years.

Many thousands of compounds can be prepared in crystalline form, but only a small fraction have been explored as detector materials. There is a need to identify semiconductor detector materials in the early stages of exploration, when samples are not available as single crystals, but only as crystalline powders. The band gaps can be estimated by measuring reflectance, but this alone does not determine which are semiconductors. The defining characteristic of a semiconductor (for circuits and nuclear detectors) is electron and hole mobility.

Thus, a semiconductor is a non-metal in which electron and hole carriers are mobile, and an insulator is a non-metal in which electrons or holes spontaneously trap. To function as a semiconductor detector both charge carriers (electrons and holes) must be mobile in an electric field. If either charge carrier is trapped by the spontaneous formation of a defect (e.g. a Vk center) in the material, the material will become polarized and ineffective as a detector. Herein are described methods and devices for the discovery and identification of new semiconductor materials based on the mobility of internally created electrons and holes.

SUMMARY OF THE INVENTION

In one embodiment, the present invention provides a method for identifying new semiconductor materials based on the mobility of internally created electrons and holes. The present method was designed for the early stages of exploration of new compounds, when samples are not available as single crystals, but as crystalline powders. In a preferred embodiment, the method comprises the steps of (1) providing a layer of a compound in crystalline powder form; (2) applying pressure to the crystalline compound to provide contact between the microcrystals in the crystalline compound; (3) applying electrical voltage and measuring the conductivity; (4) applying electrical voltage and measuring the conductivity while irradiating the compound to create electron-hole pairs; and (5) determining the ionization current due to the movement of internally generated electron and hole carriers.

In another embodiment, the present invention provides a device for applying pressure to a crystalline compound, applying electrical voltage and measuring the conductivity, repeating application of electrical voltage and measuring the conductivity while irradiating the compound to create electron-hole pairs and then determining ionization current due to the movement of internally generated electron and hole carriers.

In another embodiment, the present invention provides for new semiconductor materials BiOI, PbIF, $PbBiO_2I$, $PbBiOI$, $Pb_3O_2I_2$, $Pb_5O_4I_2$, $Bi_2GdO_4Cl$, $BiPbO_2Cl$, and $BiPbO_2Br$ discovered using the methods and devices described herein. These materials can be used for optoelectronics and radiation detectors.

In another embodiment, the present invention provides for new semiconductor materials discovered using the process and methods and pressure cell described herein.

DETAILED DESCRIPTION OF THE PREFERRED EMBODIMENT

In modern usage, semiconductor materials are valued for their ability to conduct internal electrons and holes over macroscopic distances and used as circuit elements and nuclear detectors. The present method describes a method and device for determining which materials possess this property by measuring the change in their electrical conductivity during exposure to ionizing radiation.

In accord with this and the notion that all pure inorganic materials in a specific crystal structure can be classified as either metals, semiconductors or insulators, the term "semiconductor materials" are defined herein as a non-metallic solid in which electrons and holes are mobile, and an "insulator" as a solid in which electrons or holes are self trapped. Unlike semiconductors, metals have partially filled valence bands and are electrically conductive at temperatures approaching 0 K.

In one embodiment, the present invention provides a method for identifying new semiconductor materials based on the mobility of internally created electrons and holes. The present method was designed for the early stages of exploration of new compounds, when samples are not available as single crystals, but as crystalline powders. In a preferred embodiment, the method comprises the steps of (1) providing a compound in crystalline powder form; (2) applying pressure to the crystalline compound to provide contact between the microcrystals in the crystalline compound; (3) applying electrical voltage and measuring the conductivity; (4) applying electrical voltage and measuring the conductivity while irradiating the compound to create electron-hole pairs; and (5) determining ionization current due to the movement of internally generated electron and hole carriers. The method is based on the need to determine whether these semiconductor materials have the ability to detect radiation. The final step of determining the ionization current due to the movement of internally generated electron and hole carriers is generally carried out by subtracting the ionization current measured in step 3 from the ionization current in the presence of radiation measured in step 4. The ionization current is preferably direct current ("dc") applied.

In one embodiment, the present method comprises the following steps: (1) produce powders by solid state reactions or precipitation; (2) insert powder in a pressure cell and compress with 1 ton/cm² to provide contact between microcrystals of the powder; (3) measure dc current vs. voltage without ionizing radiation; (4) measure dc current vs. voltage with 60Co ionizing radiation (450 Ci source at 8 cm, 1500 rad/min); and (5) subtract currents to determine ionization current due to the movement of internally generated electron and hole carriers. The method step (1) further comprising the step of checking the crystal phase of the crystalline powders by x-ray diffraction.

In another embodiment, the present invention provides a device for carrying out the method comprising a metal pressure cell containing two metal anvils and means for applying pressure to a thin layer of crystalline compound placed in the space between the anvils, an electrical contact to apply electrical voltage to one metal anvil, and an electrical contact on the opposite anvil to measure the conductivity across the crystalline compound, and an electrical ground. The pressure cell and the metal anvils can be made of materials such as stainless steel or titanium.

In another embodiment, the device further comprises an insulator to prevent any contacts between the two metal anvils or within the pressure cell. The insulator is preferably a non-conducting inflexible material or polymer to insure that conductivity only occurs through the crystalline compound compressed between the two anvils.

Figure 2:
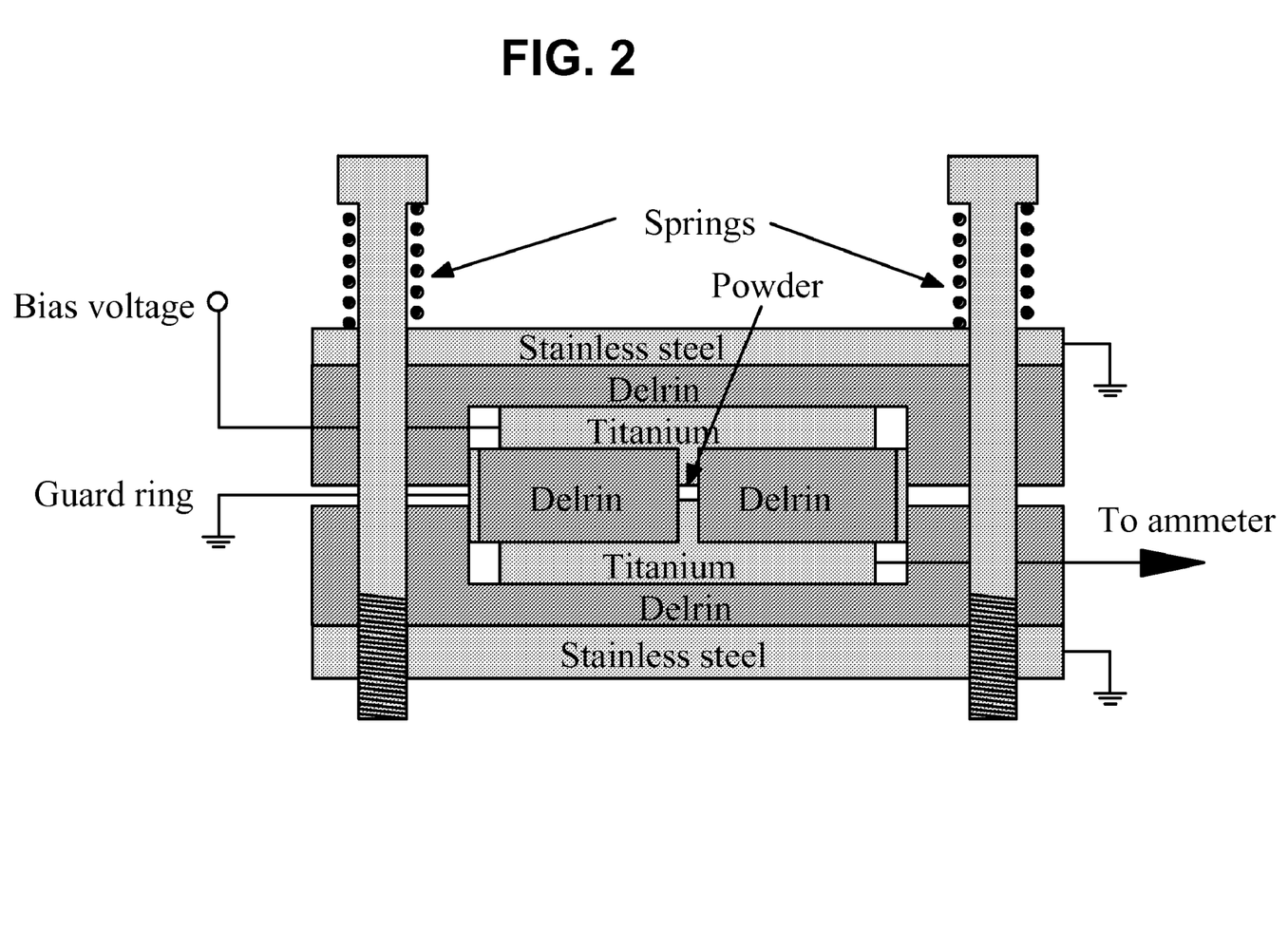
FIG. 2 is a schematic showing a cross-section or cutaway sketch of the cylindrical pressure cell used for measuring DC electrical conductivity of pressed powders. Powder is placed in the central region between 3 mm diameter titanium electrical contacts and subjected to a pressure of 0.5 N/mm².

In a preferred embodiment, the device is as shown in FIG. 2, comprising a stainless steel pressure cell containing (a) two titanium anvils encased in an inflexible non-conducting polymer, such as DELRIN (DuPont), wherein the two anvils do not make contact except at the area where the thin layer of crystalline compound is placed, (b) an electrical contact to conduct bias voltage to the first anvil, (c) an electrical contact connecting the second anvil to an ammeter, (d) an electrical ground, (e) means for applying pressure to the compound placed between the anvils, such as two large screws having springs between the screw heads and the pressure cell. The inflexible non-conducting polymer is electrically insulating and acts to confine the powder during compression.

In one embodiment, the pressure applied to the crystalline compound to provide contact between the microcrystals in the crystalline compound is at least 0.5 N/mm², preferably about 1 ton/cm². Referring to FIG. 2, the pressure cell further comprises such means for compression as screws that compress springs with a force of 30 lbs each, so the total force applied is 180 lbs to the 3 mm Titanium anvils, and the pressure is 2000 lbs (1 ton) per square cm, or 13,000 lbs per square inch.

A layer of crystalline powder is provided and placed in the pressure cell between the two anvils and compressed. In a preferred embodiment, the powder layer is 0.5-1.0 mm thick after compression; the volume is about 5-10 cubic mm and the weight of powder is about 25-50 mg.

The semiconductor materials to be tested should be provided in crystalline powder form. The powders can be produced by solid state reactions or precipitation, for example. The crystal phase of the powders can be confirmed by such methods as x-ray diffraction. X-ray diffraction measurements have been made for over 100,000 crystalline materials and the results found in the Inorganic Crystal Structure and Powder Diffraction Databases. New semiconductor materials to be tested can also be looked up these databases, synthesized and then confirmed that the correct crystalline form has been achieved by observing that the x-ray diffraction pattern is the same as provided in the database. Formulas of materials that may be prove to be semiconductor detector materials generally are high density materials (i.e., having a density of 7 or 8 or higher), possess good stopping power (e.g., stopping gamma rays), and have a high atomic number. More preferred materials possess both high density and high atomic number.

Electrical voltage is applied across the crystalline compound in the pressure cell at a range of applied voltages, and conductivity is measured. In general, the applied voltages can be from 0 volts to 100 volts. In a preferred embodiment, one electrical contact connects a direct current (dc) power supply to one anvil in the pressure cell, while another electrical contact connects the other opposite anvil to an ammeter that can measure currents as small as 1 pA.

The irradiation of the compound to create electron-hole pairs is carried out using a source for generating ionizing radiation. The amount of ionizing radiation is not critical, but measurements would be more difficult with a source having a much lower radiation activity level than about 450 Curie (Ci) or 1500 rad/min ionizing radiation. In some embodiments, it may be preferred to use a source which generates 4500 Ci. In one embodiment, the source is a Cobalt-60 cancer therapy unit used to generate gamma rays. In a preferred embodiment, the source is placed in close proximity to the pressure cell such that the crystalline compound is exposed to the ionizing radiation until equilibrium current is reached. When a source producing about 450 Ci is used, the time for exposure is about 10 minutes. In a preferred embodiment, close proximity is about 3-10 cm, more preferably, about 8 cm, depending on the strength of the source. The increase in steady-state current produced by the ionizing radiation is directly related to the mobility-lifetime product of the carrier that has the greatest trapping (usually the holes).

The step of determining ionization current due to the movement of internally generated electron and hole carriers is carried out by subtracting the measured currents to determine the ionization current due to the movement of internally generated electron and hole carriers. The current resulting from the internal generation of electrons and holes is described by the Hecht equation (K. Hecht, Zeitschrift für Physik (Berlin), 77, 235 (1932)):

$$I=I_0 d'/d[1-\exp(-d/d')]$$

where $I_0$ is the rate of electron-hole pair production and d is the sample thickness. The average drift distance before trapping is given by $d'=\mu\tau E$, where $\mu$ and $\tau$ are the carrier mobility and lifetime, respectively, and E is the electrical field strength. Detrapping and retrapping may occur, increasing the effective carrier lifetime $\tau$. In a crystalline semiconductor powder most of the carriers recombine in the material, and $d' \ll d$, whereby the equation reduces to $I=I_0$, $d'/d=I_0\mu\tau V/d^2$. Thus, if trapping is negligible, $d' \gg d$ and $I \approx I_0$. If trapping is severe, $d' \ll d$ and $I \approx I_0[d'/d]=I_0 \mu t V/d^2$. If either carrier self traps, $d' \approx 0$ and $I \approx 0$. In an insulator, $d'=0$ and $I=0$.

Although carrier trapping is severe in semiconductor powder samples, if the rate of internal generation of electrons and hold is sufficiently high, the resulting steady state conductivity can be measured. On the other hand, if even one carrier is self-trapped, the internally generated carriers are not mobile and steady-state conductivity is negligible.

The ionization current measured for semiconductors has little quantitative significance, since there can be severe trapping on microcrystal surfaces, however, the present methods and devices are intended for use in screening new semiconductor materials. Some semiconductor samples may have such severe trapping that the ionization current is not measurable, however such severe trapping could indicate a sample not worthy of further investigation. Furthermore, it may be difficult to measure the ionization current in samples with high background current (e.g. ionic conductivity). For example, there may exist samples where radiation damage increases the ionic conductivity, although this has not yet been observed.

Semiconductor materials discovered by this process can then be evaluated using known methods in the art of purification, synthesis and crystallization for obtaining crystals useful as detector materials.

In a preferred embodiment, the present invention provides for new semiconductor materials useful for detecting radiation, discovered using the methods and device described herein. In a specific embodiment, the new semiconductor materials discovered using the methods and pressure cell described herein are BiOI, PbIF, $BiPbO_2I$, PbBiOI, $Pb_3O_2I_2$, $Pb_5O_4I_2$, $Bi_2GdO_4Cl$, $BiPbO_2Cl$, and $BiPbO_2Br$.

Example 1

Figure 1:
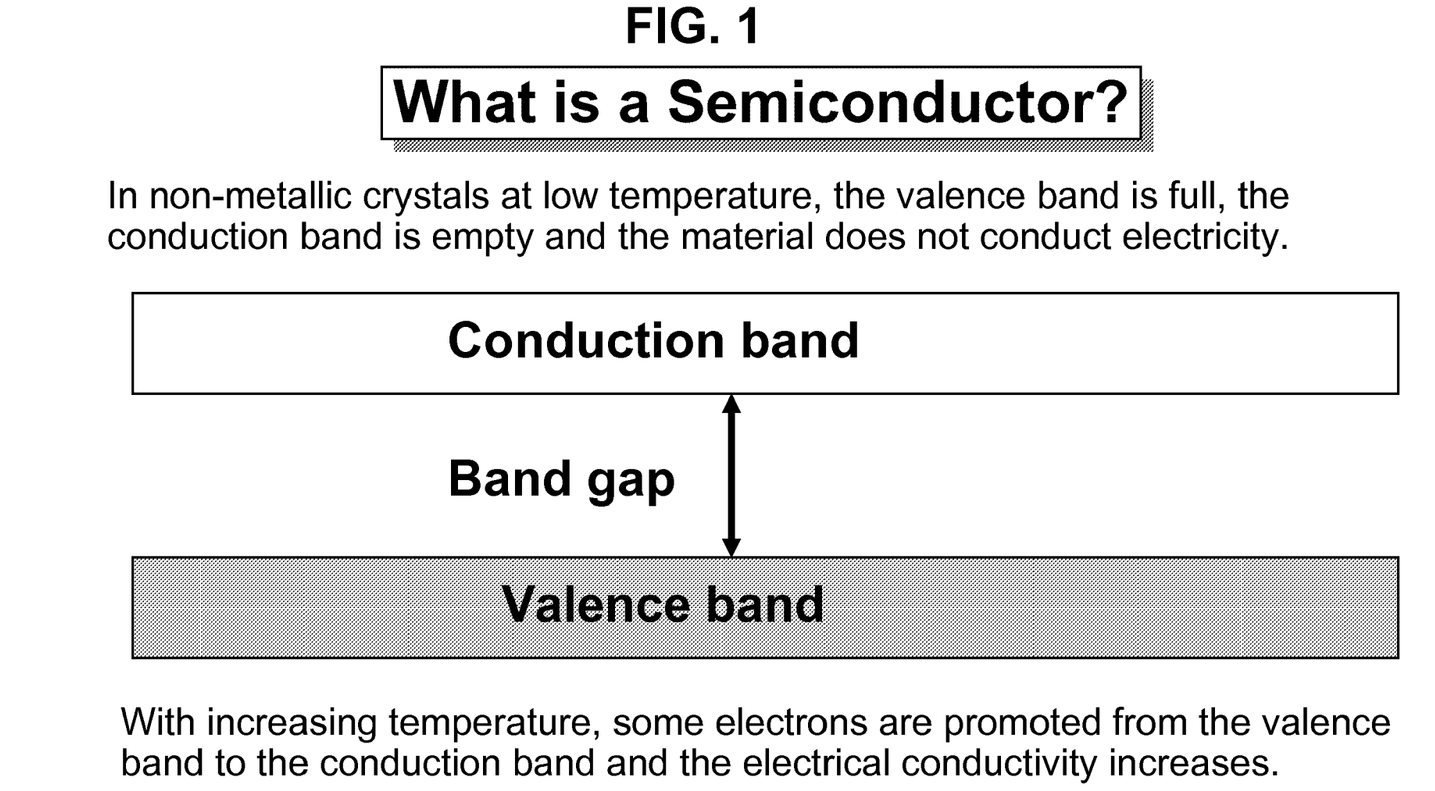
FIG. 1 is schematic showing the characteristics of a semiconductor.

Pressure cell and Validation of the DC Ionization Conductivity Methods Using Known Semiconductor Materials and True Insulators In this example we placed the sample between two titanium anvils in a pressure cell as shown in FIG. 1 and the electrical conductivity is measured for a range of applied voltages. The measurements were then repeated during irradiation by 1.2 MeV gamma rays from a 450 Curie Co-60 cancer therapy unit placed 8 cm from the cell for about 10 minutes, the amount of time for equilibrium current to be reached.

The measurements were taken without radiation present (OFF) and during irradiation by the Co-60 source (ON). The difference in the ionization current in the present of radiation can be observed in the graph. It is this difference in height that is plotted on the graphs shown in FIGS. 5, 6 and 8. After the voltage is applied the material polarizes and reaches a steady current. When the source is turned on, traps fill and the current increases to an equilibrium level. At this point, the rate of generation of electron-hole pairs is equal to the rate of trapping and recombination. When the source is removed the current drops to the initial level as the carriers detrap.

The samples used were either the highest purity materials obtained from chemical suppliers or synthesized in our laboratory from highest purity available starting materials. For all samples the crystal phase was checked by x-ray diffraction and a weighed amount was used to produce a compressed thickness of approximately 1 mm (volume 7 $mm^3$).

After a powder sample is pressed between the titanium anvils, the electrical conductivity is measured for a range of applied voltages (source off) and then the measurements are repeated during irradiation by 1.2 MeV Co-60 gamma rays from a 450 Ci cancer therapy unit (source on). The dose rate was 1,500 rad/min. The currents were measured using a Keithley model 617 electrometer.

Figure 3:
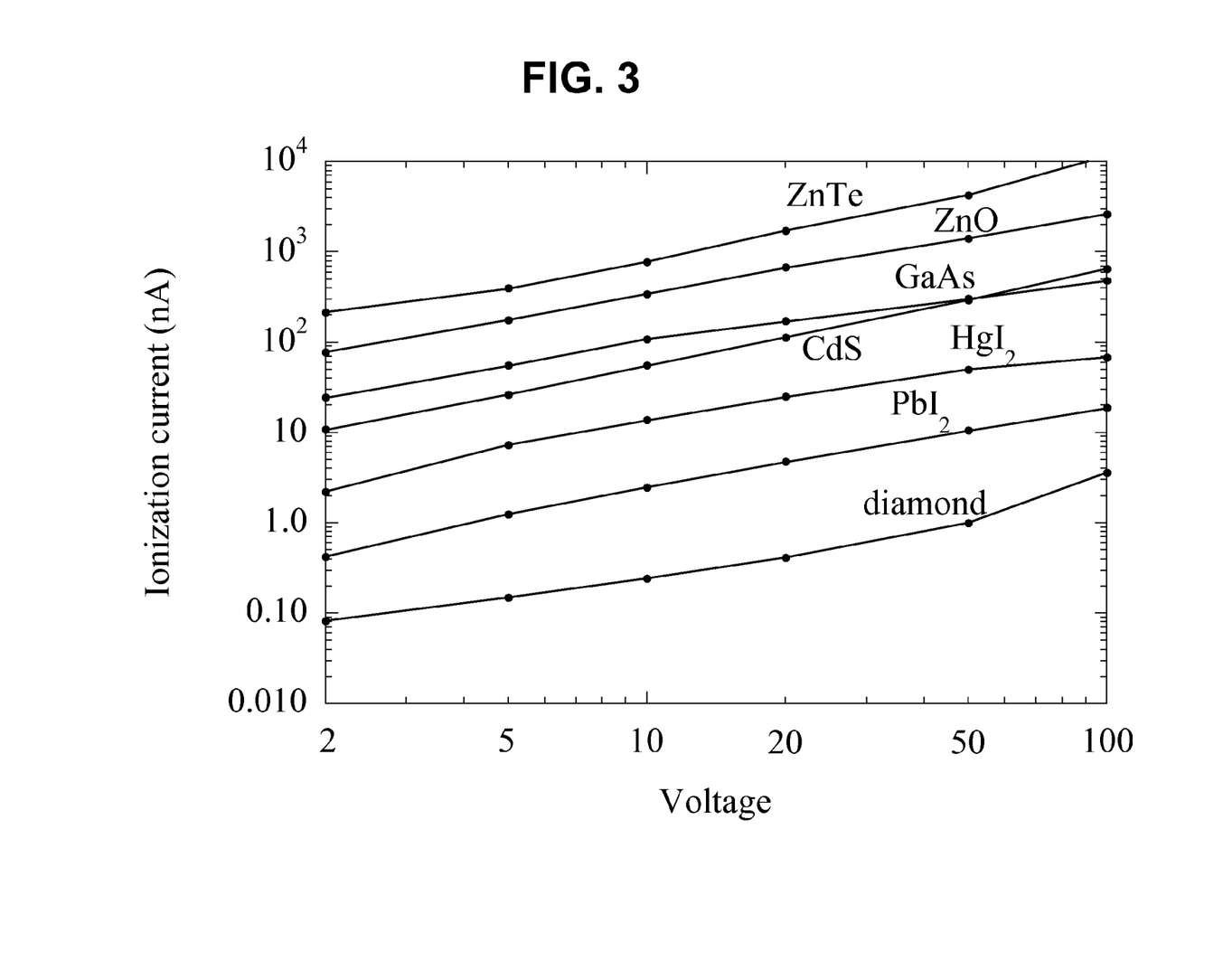
FIG. 3 is a graph showing the dc ionization current [I(on)–I(off)] as a function of voltage measured for known semiconductors. Experimental uncertainties in current are approximately 10%+0.02 nA.

FIG. 3 shows the source-dependent steady-state currents of the known semiconductors ZnO (band gap 3.37 eV), CdS (2.49 eV), ZnTe (2.3 eV), GaAs (1.5 eV), $HgI_2$ (2.2 eV), $PbI_2$ (2.5 eV) and diamond (5.4 eV) increases linearly with applied voltage as expected. All currents reported here are steady state values. The relationship between ionization current and voltage is nearly linear as expected from the Hecht equation for the case where $d' \ll d$. The numbers in the parentheses are the accepted room-temperature energy gaps. The relationship is linear as expected from the Hecht equation for the case where $d' \ll d$. Variations between samples are due to differences in $\mu\tau$ products. Since most of the trapping is on the microcrystal surfaces, the observed current values are not indicative of what would be collected from single crystals.

Figure 4:
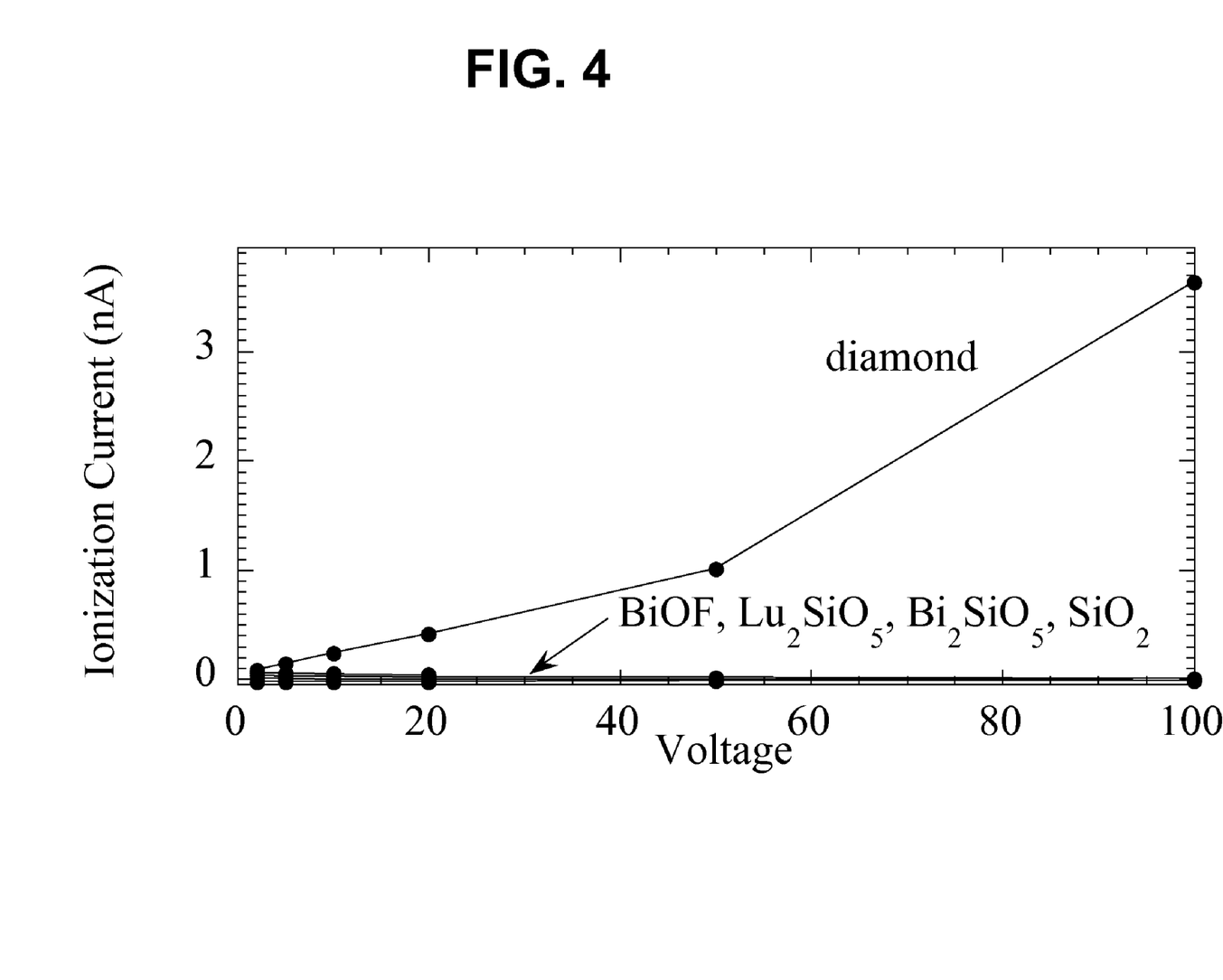
FIG. 4 is a graph showing the dc ionization current [I(on)–I(off)] as a function of voltage is not measurable for true insulators. Diamond is shown as a reference. Note: In insulators, ionizing radiation can put electrons into the conduction band but the resulting current is a transient and not a dc current.

Referring now to FIG. 4, the corresponding current of true insulators BiOF, $Lu_2SiO_5$, $Bi_2SiO_5$, $SiO_2$, and are consistent with zero. No measurable current is shown.

Tables I lists the density, experimentally measured band gap and currents I(off) and I(on) measured at 100 V with the source off and on, respectively for materials studied in which the materials were not identified as semiconductors. Table I lists materials whose ionization current is too small to be identified as semiconductors. Band gaps were taken from W. H. Strehlow and E. L. Cook, "Compilation of energy band gaps in elemental and binary compound semiconductors and insulators," J Phys Chem Ref Data, vol. 2, pp. 163-199, 1973, or were determined in our laboratory from measurements of reflectance vs. wavelength. While hole hopping is known to occur for CsI, the resulting current is well below those in Table II.

TABLE I

MATERIALS NOT IDENTIFIED AS SEMICONDUCTORS

| Compound | ρ (gm/cm³) | $E_G$ (eV) | I(off)[a] (nA) | I(on)[b] (nA) |
|---|---|---|---|---|
| $Bi_4Ge_3O_{12}$ | 7.1 | 4.2 | 2.50 | 2.51 |
| $Bi_2SiO_5$ | 7.9 | | 0.14 | 0.16 |
| BiOF | 9.2 | | 74.7 | 74.6 |
| CsI | 4.7 | 6.2 | 0.58 | 0.67 |
| $Lu_2SiO_5$ | 7.4 | 6.4 | 1.43 | 1.40 |
| $PbBr_2$ | 6.7 | 3.2 | 1097 | 1093 |
| $PbCl_2$ | 5.9 | 3.9 | 113 | 110 |
| $PbF_2$ | 7.8 | 5.0 | 1150 | 1151 |
| $SiO_2$ | 2.6 | 8.4 | 1.01 | 1.02 |

Example 2

DC Ionization Conductivity Methods Used to Identify New Semiconductor Materials

Figure 5:
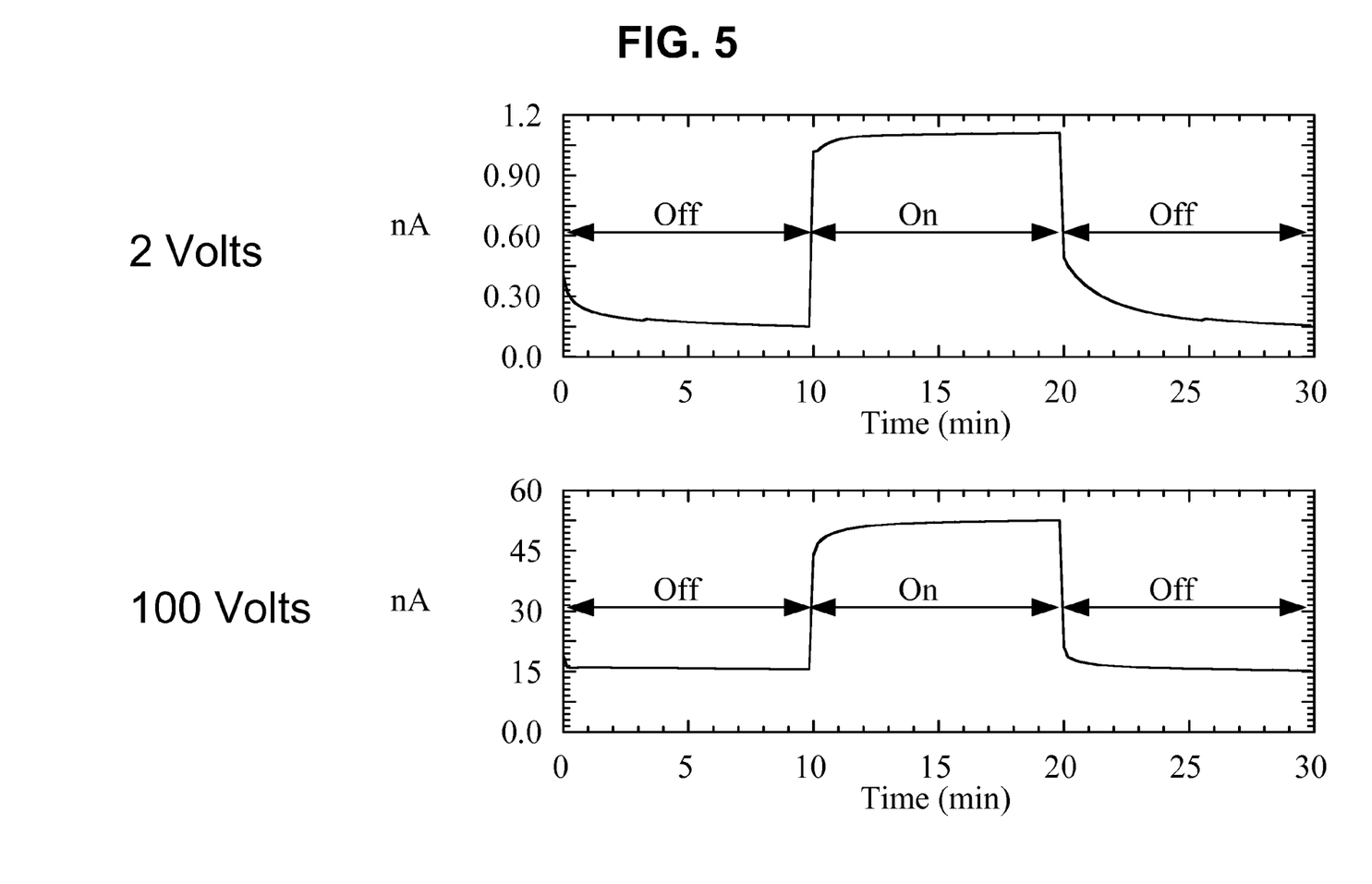
FIG. 5 is a graph showing the ionization current as a function of time measured for new semiconductor material $PbBiO_2Cl$.

Referring now to FIG. 5, using the device of Example 1, the sample of crystalline $BiPbO_2Cl$ was placed between two titanium anvils in a pressure cell as shown in FIG. 2 and the electrical conductivity is measured at the applied voltages of 2V and 100V as a function of time.

Tables II also lists the density, experimentally measured band gap and currents I(off) and I(on) measured at 100 V with the source off and on, respectively for materials studied in which the materials were identified as semiconductors. In Table II many materials exhibit significant I(off) values due to ionic conduction and n- or p-type doping. The large currents seen for the semiconductors ZnO and ZnTe are due to the latter. Band gaps were taken from W. H. Strehlow and E. L. Cook, "Compilation of energy band gaps in elemental and binary compound semiconductors and insulators," J Phys Chem Ref Data, vol. 2, pp. 163-199, 1973, or were determined in our laboratory from measurements of reflectance vs. wavelength.

Table II lists materials whose ionization current increases with voltage and thereby identified as semiconductors.

TABLE II

MATERIALS IDENTIFIED AS SEMICONDUCTORS

| Compound | ρ (gm/cm³) | $E_G$ (eV) | I(off)[a] (nA) | I(on)[b] (nA) |
|---|---|---|---|---|
| *$BiGdO_4Cl$ | 8.4 | 2.7 | 733 | 904 |
| *$BiPbO_2Cl$ | 8.3 | 2.7 | 14.3 | 52.7 |
| *$BiPbO_2Br$ | 8.6 | 2.8 | 17.5 | 25.3 |

TABLE II-continued

MATERIALS IDENTIFIED AS SEMICONDUCTORS

| Compound | ρ (gm/cm³) | $E_G$ (eV) | I(off)[a] (nA) | I(on)[b] (nA) |
|---|---|---|---|---|
| *$BiPbO_2I$ | 8.6 | 2.7 | 6.1 | 703 |
| *BiOI | 8.1 | 2.1 | 1.80 | 4.11 |
| CdS | 4.8 | 2.5 | 4.9 | 650 |
| diamond | 3.5 | 5.4 | 0.04 | 3.6 |
| GaAs | 5.3 | 1.5 | 1417 | 1894 |
| $HgI_2$ | 6.4 | 2.2 | 10.4 | 78 |
| *$Pb_3O_2I_2$ | 7.6 | 2.7 | 2.5 | 27 |
| *$Pb_5O_4I_2$ | | 2.7 | 0.81 | 1.24 |
| *PbFI | 7.4 | 3.0 | 5.5 | 9.3 |
| $PbI_2$ | 6.1 | 2.5 | 4.0 | 22.6 |
| PbO | 9.6 | 2.7 | 0.31 | 2.37 |
| ZnO | 5.7 | 3.4 | 10,500 | 13,100 |
| ZnS | 4.1 | 3.8 | 5.07 | 5.59 |
| ZnTe | 5.8 | 2.3 | 482,000 | 493,000 |

Figure 6:
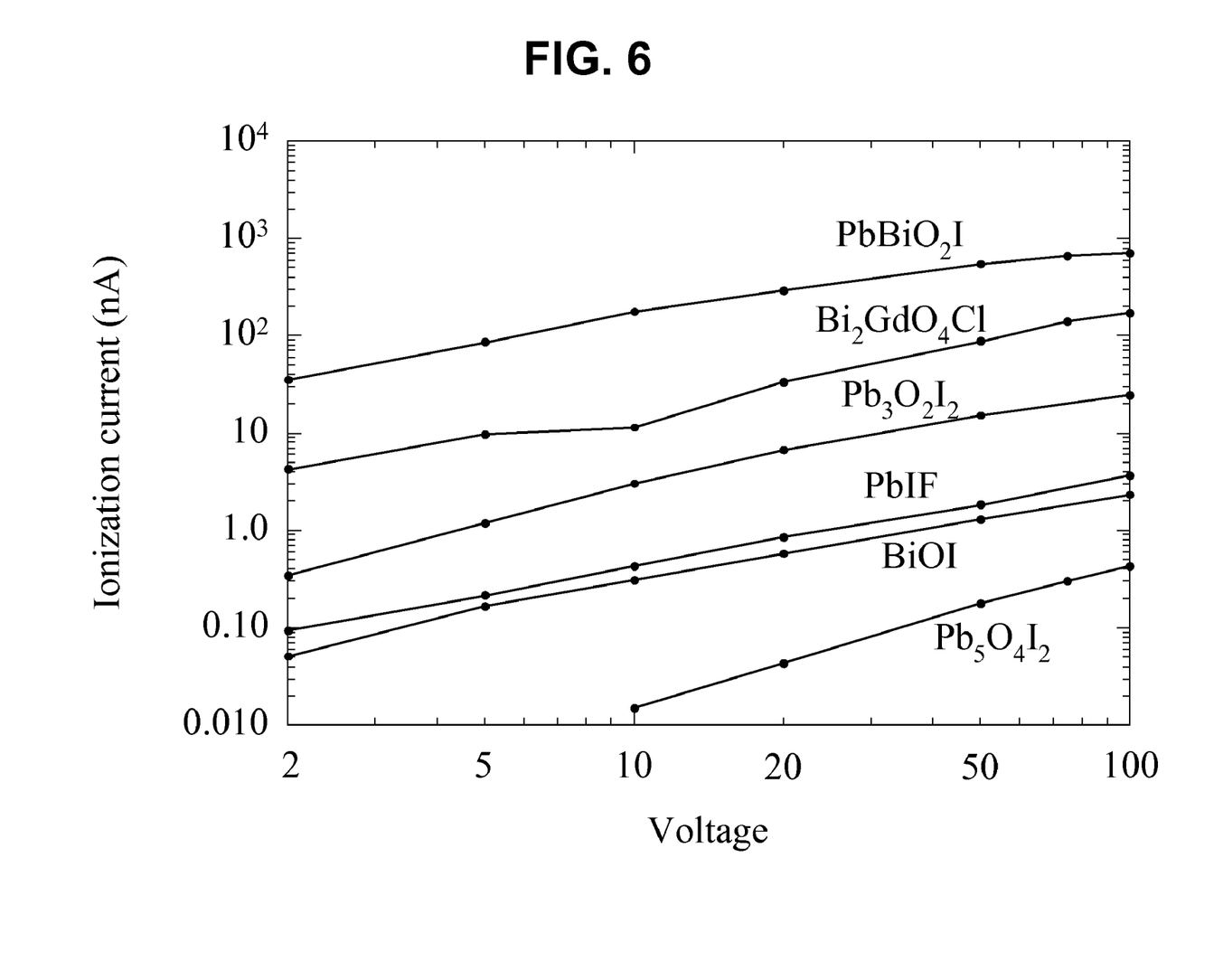
FIG. 6 is a plot showing the dc ionization current [I(on)–I(off)] measured as a function of applied voltage for new semiconductor materials: $BiOI$, $PbIF$, $PbBiO_2I$, $PbBiOI$, $Pb_3O_2I_2$, $Pb_5O_4I_2$, $Bi_2GdO_4Cl$, $BiPbO_2Cl$, and $BiPbO_2Br$. Experimental uncertainties in current are approximately 10%+0.02 nA

*New determination as semiconductors
[a]Current at 100 V with source off
[b]Current at 100 V with source on Table II also shows the raw data in table format of the ionization current measured at a 100V for various materials, without radiation present (I(off)) and during irradiation (I(on)). The difference between the measured conductivity with the radiation OFF or ON is shown. The formula of the compound and its identity as a semiconductor as determined by the process is indicated by the asterisk. The other materials were not identified as a semiconductor material by the method. The measured current for each material (e.g., I(on) and I(off)) at the various voltages is not shown. However, FIG. 6 shows the ionization current (I(on)–I(off)) measured at various voltages as a function of voltage for new semiconductor materials: BiOI, PbIF, $PbBiO_2I$, PbBiOI, $Pb_3O_2I_2$, $Pb_5O_4I_2$, $Bi_2GdO_4Cl$, $BiPbO_2Cl$, and $BiPbO_2Br$. Because this method uses the difference between the source on and source off conditions, it cannot be used for samples whose ionic conductivity is much larger than the ionization conductivity.

The present structures, embodiments, examples, methods, and procedures are meant to exemplify and illustrate the invention and should in no way be seen as limiting the scope of the invention. Various modifications and variations of the described pressure cell, methods of making, and applications and uses thereof of the invention will be apparent to those skilled in the art without departing from the scope and spirit of the invention.

Any patents or publications mentioned in this specification are indicative of levels of those skilled in the art to which the invention pertains and are hereby incorporated by reference to the same extent as if each was specifically and individually incorporated by reference.

What is claimed is:

1. A method for identifying new semiconductor materials based on the mobility of internally created electrons and holes, comprising the steps of:
    (a) providing a layer of compound in crystalline powder form;
    (b) applying pressure to the crystalline compound to provide contact between microcrystals in the crystalline compound;
    (c) applying electrical voltage and measuring the conductivity without radiation;
    (d) applying electrical voltage and measuring the conductivity in the presence of radiation to create electron-hole pairs in the crystalline compound; and (e) determining the ionization current due to the movement of internally generated electron and hole carriers.

2. The method of claim 1, wherein final determining step e is carried out by subtracting the ionization current measured in step c from the ionization current in the presence of radiation measured in step d.

3. The method of claim 1, wherein the voltage applied is from 0 to 100 volts.

4. The method of claim 1, wherein the radiation is at least 450 Curie.

5. The method of claim 1, wherein the layer of crystalline compound is about 0.5 to 1 mm thick after compression.

6. The method of claim 1, wherein the pressure applied to the compound is at least 0.5 N/mm$^2$.

7. A method for measuring movement of internally generated electron and hole carriers in a material comprising the steps of: (1) producing powders by solid state reactions or precipitation; (2) inserting powder in a pressure cell and compress with 1 ton/cm$^2$ to provide contact between microcrystals of the powder; (3) measuring dc current vs. voltage without ionizing radiation; (4) measuring dc current vs. voltage with ionizing radiation; and (5) subtracting currents to determine ionization current due to the movement of internally generated electron and hole carriers.

8. The method of claim 7, wherein step (1) further comprising the step of checking the crystal phase of the crystalline powders by x-ray diffraction.

9. The method of claim 7, wherein the ionizing radiation is generated by a 450 Ci $^{60}$Co source at 8 cm from the material, at 1500 rad/min.

* * * * *